(12) United States Patent
Van Dun et al.

(10) Patent No.: US 7,803,600 B2
(45) Date of Patent: Sep. 28, 2010

(54) *MICROMONOSPORA* SPECIES THAT PRODUCES A BAFILOMYCIN-LIKE METABOLITE

(75) Inventors: Jacobus Alphonsus Josephus Van Dun, Kasterlee (BE); Walter Boudewijn Leopold Wouters, Kapellen (BE); Michel Marie François Janicot, Mol (BE); Ursula Maria Mocek, Bellevue, WA (US); Jodi Ann Laakso, North Bend, WA (US)

(73) Assignee: Janssen Pharmaceutica N.V., Beerse (BE)

( * ) Notice: Subject to any disclaimer, the term of this patent is extended or adjusted under 35 U.S.C. 154(b) by 713 days.

(21) Appl. No.: 11/684,806

(22) Filed: Mar. 12, 2007

(65) Prior Publication Data

US 2007/0148744 A1    Jun. 28, 2007

Related U.S. Application Data

(62) Division of application No. 10/517,788, filed as application No. PCT/EP03/50276 on Jun. 30, 2003, now Pat. No. 7,214,705.

(60) Provisional application No. 60/393,149, filed on Jul. 2, 2002.

(51) Int. Cl.
*C12N 1/20* (2006.01)
(52) U.S. Cl. .................................... 435/252.1
(58) Field of Classification Search ........................ None
See application file for complete search history.

(56) References Cited

U.S. PATENT DOCUMENTS 4,558,139 A    12/1985    Hagenmaier et al.

FOREIGN PATENT DOCUMENTS

| EP | 0 689 839 | | 1/1996 |
|---|---|---|---|
| EP | 0689839 | * | 1/1996 |
| WO | WO 93/18652 | | 9/1993 |
| WO | WO 01/02413 | | 1/2001 |

OTHER PUBLICATIONS

Laasko et al., The Journal of Antibiotics, vol. 56 No. 11, Nov. 2003, pp. 909-916.*
Ohta et al., Tetrahedron Letters 42 (2001) 4179-4181.*
Mosmann et al., "Rapid Colorimetric Assay for Cellular Growth and Survival: Application to Proliferation and Cytotoxicity Assays," *Journal of Immunological Methods*, 1983; 65(1-2):55-63.

O'Shea et al., "Absolute Configurations of Macrolide Antibiotics of the Bafilomycin and Leucanicidin Groups," *The Journal of Antibiotics*, 1997; 50(12):1073-1077.
Werner et al., "Metabolic Products of Microorganisms. 224[†] Bafilomycins, a New Group of Macrolide Antibiotics Production, Isolation, Chemical Structure and Biological Activity," *The Journal of Antibiotics*, 1984; 37(2):110-117.
In the U.S. Patent and Trademark Office, Non-Final Office Action in re: U.S. Appl. No. 10/517,788, dated Mar. 21, 2006, 13 pages.
In the U.S. Patent and Trademark Office, Non-Final Office Action in re: U.S. Appl. No. 10/517,788, dated Aug. 15, 2006, 6 pages.

* cited by examiner

*Primary Examiner*—Irene Marx
(74) *Attorney, Agent, or Firm*—Patton Boggs LLP

(57) ABSTRACT

The invention provides a compound of formula (I) and pharmaceutically acceptable salts thereof. Processes for the isolating of this bafilomycin metabolite from a novel *Micromonospora* species, pharmaceutical compositions containing this metabolite and methods of treatment using said metabolite are also described.

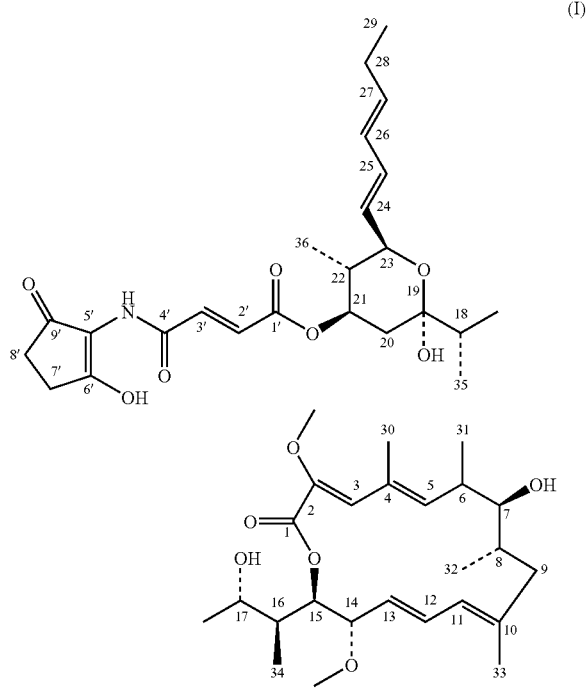

2 Claims, 4 Drawing Sheets

MICROMONOSPORA SPECIES THAT PRODUCES A BAFILOMYCIN-LIKE METABOLITE

CROSS REFERENCE TO RELATED APPLICATIONS

This case is a divisional application of U.S. patent application Ser. No. 10/517,788 filed Dec. 14, 2004, now U.S. Pat. No. 7,214,705 which claims the benefit of a 371 of international application serial number PCT/EP03/50276 filed on Jun. 30, 2003, which claims the benefit of provisional application 60/393,149 filed on Jul. 2, 2002, the contents of which are all incorporated by reference in their entirety.

The present invention relates to a novel bafilomycin-like metabolite isolated from a novel *micromonospora* species having potent antiproliferative activity as well as to processes for isolating said metabolite, pharmaceutical compositions containing this metabolite and methods of treatment using said metabolite.

Although the increasing basic knowledge of major cellular signaling pathways has allowed recent discovery of promising "targeted therapeutics" to help fighting cancer (e.g., inhibitors of farnesyltransferase, growth factor receptor tyrosine kinases, Bcr/abl, etc. . . . ), more classical cytotoxics still remain an important part of the foundation of an oncology product portfolio in the modern pharmaceutical industry. The partial success of traditional cancer cytotoxic chemotherapy stems in large part from agents derived from natural sources.

Macrolides are a group of antibiotics that includes natural members. Most of the macrolides are produced by *Streptomyces* spp. bacteria. However also macrolides produced by *Micromonospora* spp. are known. Macrolides are characterised in that they are composed of a large aglycone ring (from 14-16 carbon atoms) to which are attached several sugars. A special series of these macrolides are the bafilomycins. These compounds share the structural feature of having a 16-membered macrocyclic lactone ring and one or two side-chain sugars. The aforementioned bafilomycins were previously known to have activity as antiparasitics, antithelmintics, antibiotics, insecticides, antifungals, agents for the therapy of bone diseases and as vacuolar-type ATPase proton pump (v-ATPase) inhibitors. Later on, it has been found that, when run through whole tumour-cell assays, compounds from this group exhibit antitumour activity.

WO 01/02413 discloses bafilomycin derivatives of formula (II),

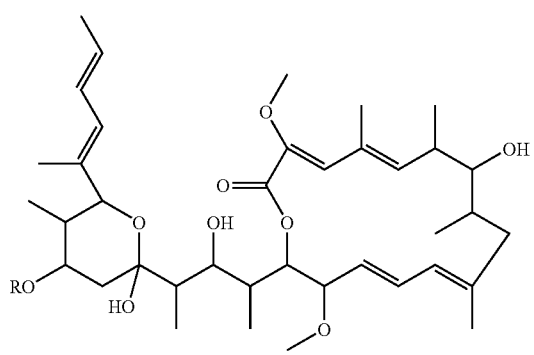

wherein R is —H or —CO—CH═CH—COOH, and pharmaceutically acceptable salts and esters thereof. The compounds display activity against tumour growth in mammals. WO 01/02413 further provides a method for the treatment or prophylaxis of tumour invasion by administration of compounds of formula (II) or of known macrolide compounds.

The present invention encompasses a novel structure of formula (I), a tautomer thereof, or a pharmaceutically acceptable salt thereof, with a new hexadiene sidechain at C23. The compound of formula (I) shows antiproliferative activity and is most unlikely a substrate for P-glycoprotein and/or Multidrug Resistant Protein.

The compound of formula (I) is a new bafilomycin-like derivative isolated from liquid fermentation cultures of novel actinomycetes of the genus *Micromonospora*.

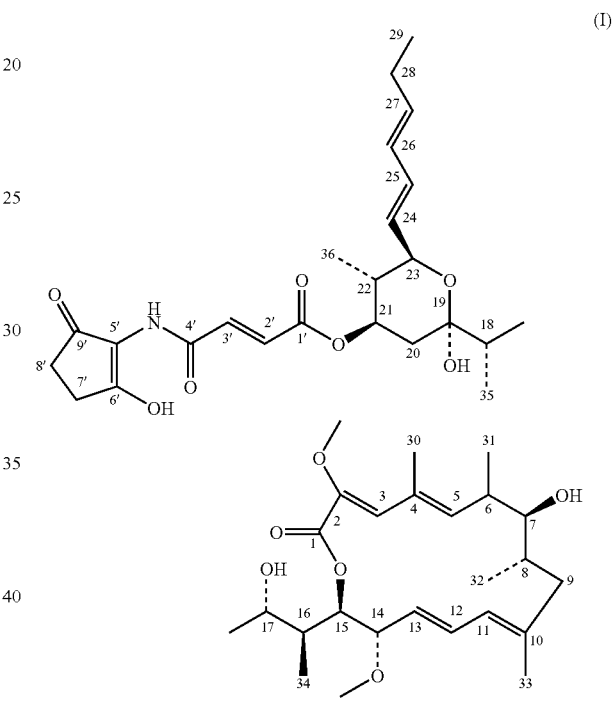

The compound of formula (I) was extensively characterized for its ability to inhibit tumour cell growth. The dose-dependent inhibition of the compound of formula (I) in four selected tumour cell proliferation assays was typical for classical cytotoxics, with very steep and narrow dose-response curves. Initial observation on inhibition of tumour cell proliferation was extended to a wide variety of human tumour cell lines, from ovary, prostate, pancreas, colon and lung origins, with observed $IC_{50}$ values in the nM range of concentrations.

Multi-drug resistance is considered as one of the major elements in the failure of anticancer therapeutics in clinical trials. Tumours become resistant to therapeutic agents by overexpression of both P-glycoprotein and Multidrug Resistant Protein which represent the major elements of the Multidrug Resistant system. Moreover, the constitutive expression of P-glycoprotein in the intestinal epithelium will, in case of oral administration, markedly reduce absorption when the compound is a substrate for the P-glycoprotein. The activity of the compound of formula (I) on P-glycoprotein or Multidrug Resistant Protein-expressing tumour cell lines and respective parental cells, was compared to that of a known substrate for P-glycoprotein/Multidrug Resistant Protein, adriamycin. The compound of formula (I) inhibited cell proliferation in the nM range of concentrations regardless of the P-glycoprotein and/or Multidrug Resistant Protein expression status. These results strongly suggest that there is no substantial recognition of the compound of formula (I) by the P-glycoprotein and Multidrug Resistant Protein pump proteins.

The present novel cancer therapeutic agent shows, like most members of this class of compounds, some acute toxicity at higher concentrations. Persons skilled in the art will however be able to determine an appropriate therapeutic range depending upon the condition of the patient.

Pharmaceutically acceptable addition salts encompass pharmaceutically acceptable acid addition salts and pharmaceutically acceptable base addition salts. The compound of formula (I) having basic properties may be converted in its pharmaceutically acceptable acid addition salts by treating it with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The compound of formula (I) having acidic properties may be converted in its pharmaceutically acceptable base addition salt by treating it with a suitable organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "acid or base addition salts" also comprises the hydrates and the solvent addition forms which the compound of formula (I) is able to form. Examples of such forms are e.g. hydrates, alcoholates and the like.

The structure encompasses several carbonyl groups. These carbonyl groups may give rise to what is generally referred to as keto-enol tautomerism. As an example there is shown hereunder the keto-enol tautomers that are in equilibrium. For simple aliphatic ketones there is very little of the enol form present at equilibrium. But in other instances the enol form can be present in higher concentration.

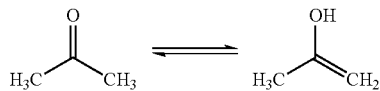

Tautomerism is a type of isomerism where the isomers only differ by the placement of a proton and the corresponding location of the double bond. The isomers which in solution are in equilibrium are called tautomers.

It should be clear that any tautomer of the present structure is meant to be included in the scope of the present application.

This invention also provides a method for inhibiting tumour growth, a method for the treatment of cancer, by administering an effective amount of the compound of the present invention, to a subject, e.g. a mammal (and more particularly a human) in need of such treatment. Examples of cancer types which may be inhibited, but are not limited to solid and haematological cancers, leukemia, skin cancers such as melanoma and basal cell carcinoma, renal cancer, lung cancer such as small cell lung cancer, non-small-cell lung cancer and alveolar cell carcinoma, colon cancer, breast cancer, prostate cancer, pancreatic cancer, stomach cancer, medullary thyroid cancer, brain cancers and head/neck cancers.

These compounds may also be useful in the treatment of neurofibromatosis, reumathoid arthritis, restenosis and other proliferative diseases.

The present compound, in view of its antibacterial characteristics, is also useful as an antibacterial medicine. This invention also provides a method for treating bacterial infections, by administering an effective amount of the compound of the present invention, to a subject, e.g. a mammal (and more particularly a human) in need of such treatment.

The present invention discloses the compound of formula (I) for use as a medicine as well as the use of these compounds of formula (I) for the manufacture of a medicament for inhibiting tumour growth.

In view of its useful pharmacological properties, the subject compound may be formulated into various pharmaceutical forms for administration purposes.

To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient, calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those skilled in the art could easily determine the effective amount from the test results presented hereinafter. In general it is contemplated that a therapeutically effective amount would be from 0.001 mg/kg to 100 mg/kg body weight, and in particular from 0.5 mg/kg to 100 mg/kg body weight. It may be appropriate to administer the required dose as two, three, four or more sub-doses at appropriate intervals throughout the day. Said sub-doses may be formulated as unit dosage forms, for example, containing 0.5 to 500 mg, and in particular 10 mg to 500 mg of active ingredient per unit dosage form.

EXPERIMENTAL PART

Figure 1A:
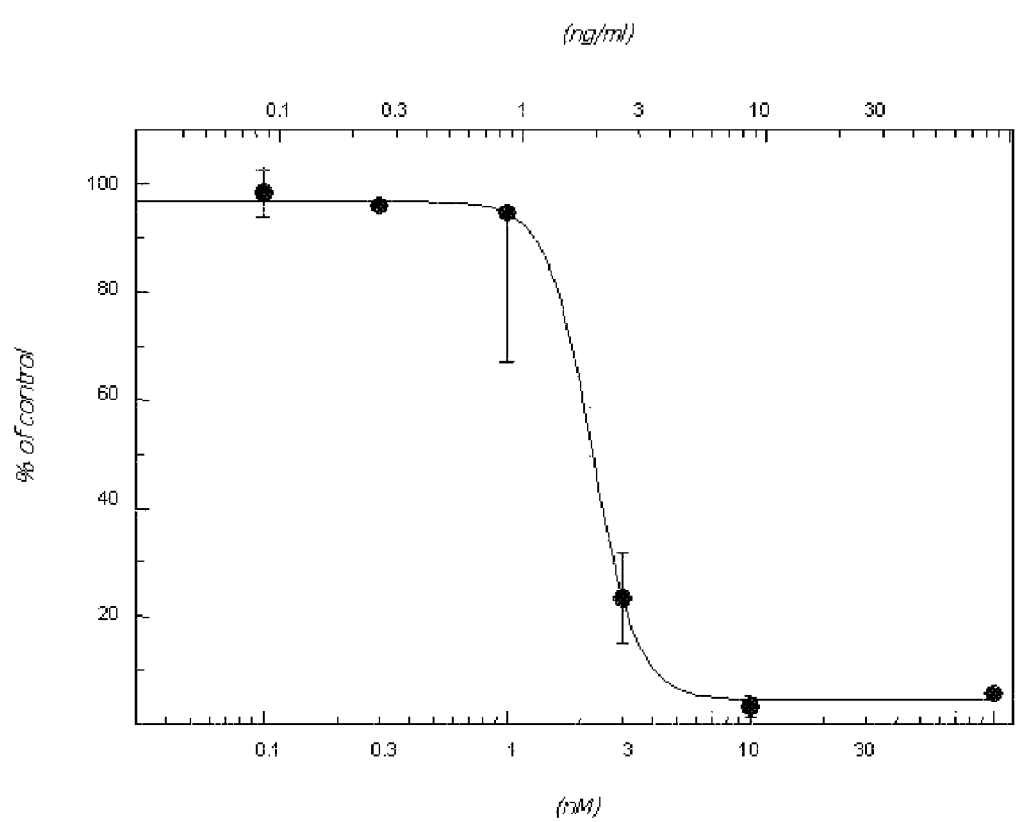
FIG. 1A: Dose-dependent inhibition of tumour cell proliferation (bioassay) by the compound of formula (I). Human MCF-7 tumour cells were treated with indicated concentrations of the compound of formula (I) for 4 days. Results, expressed as % of control untreated cells, are the mean±SE of at least 3 different experiments.

In the course of a screening program designed to identify new antitumour compounds (cytotoxics), a new bafilomycin-like metabolite was isolated. The same metabolite was isolated from liquid fermentation cultures of two different *actinomycete* of the genus *Micromonospora*. *Micromonospora* spp. JS1035 was isolated from river sediments from Sombo, Cameroon while *Micromonospora* spp. JS1044 was isolated from river sediments from Mundemba, Cameroon. As soon as it was detected that both strains produced the same active compound it was decided to further characterize the compound present in liquid fermentation cultures from *Micromonospora* spp. JS1035. A culture of each micro-organism utilised for the production of these new macrolide have been deposited (May 29, 2002) in the Laboratory for Microbiology in the Belgian Coordinated Collections of Microorganism at the University of Gent, Gent, Belgium, under accession number LMG P-21525 for *Micromonospora* spp. JS1035 and under accession number LMG P-21526 for *Micromonospora* spp. JS1044. These deposits have been made under the provisions of the Budapest Treaty on the International Recognition of the Deposit of Microorganisms for the Purposes of Patent Procedure and all restrictions on the availability thereof to the public will be irrevocably removed upon granting of a patent on this application.

General

Fermentation and Isolation

Liquid fermentation cultures of *Micromonospora* spp. JS1035 were extracted with ethyl acetate to yield the crude extract that was subsequently purified using counter current partition chromatography (CPC). Pure material for structure elucidation was obtained after two consecutive CPC fractionations using different conditions. Mass spectral analysis (see Table 1) of this material indicated a molecular weight of 853 and a molecular formula of $C_{47}H_{67}NO_{13}$.

TABLE 1

Physico-chemical properties of the compound of formula (I).

| | |
|---|---|
| Appearance | Light brown solid |
| Melting Point | 114-120°C. |
| $[\alpha]^{25}_D$ | −38.0 (c 0.1, MeOH) |
| Molecular Formula | $C_{47}H_{67}NO_{13}$ |
| Pos. ESI*-MS | 854 $(M + H)^+$ |
| HRFAB*-MS (m/z) | Found: 876.4514 |
| | Calcd: 876.4510 (for $C_{47}H_{67}NO_{13}Na$) |
| UV (MeOH) $\lambda_{max}$ nm ($\epsilon$) | 233, 286, 345 |
| IR* $\nu_{max}$ (film) cm$^{-1}$ | 3408, 2923, 1717, 1687, 1614, 1247, 1097, 751 |

*ESI: Electron Spray Ionisation, HRFAB: High Resolution Fast Atom Bombardment, IR: Inversion Recovery Structure Determination The NMR data for the compound of formula (I) was initially obtained in $CDCl_3$. However, it was soon discovered that the compound of formula (I) was not stable in this solvent. Subsequent NMR work was performed using acetone-$d_6$ and yielded a complex proton NMR spectrum. A full set of NMR experiments including $^{13}C$ NMR, Distortionless Enhancement by Polarization Transfer (DEPT), Correlated Spectroscopy (COSY), Heteronuclear Multiple Quantum Coherence (HMQC), and Heteronuclear Multiple Band Coherence (HMBC) was obtained.

Assembling the partial structures for the compound of formula (I) was straightforward. The NMR data (Table 2) for the macrolide, C16-C23, and C1'-C4' were in good agreement with published data. (Werner G. et al. J. Antibiotics 37: 110-117, 1984)

Attachment of the new hexadiene sidechain (C24-C29) was accomplished by careful study of the correlations between relevant atoms. For instance, H24 showed an HMBC correlation to C22 and C23, and H25 also showed an HMBC correlation to C23. The COSY data were also consistent with placement of the new sidechain at C23. Several $^{13}C$ NMR signals (C5', C6', and C9') corresponding to the cyclopentenone ring were obscured in the $^{13}C$ NMR spectrum, probably due to the presence of resonance structures between the vinylic OH and the carbonyl group.

Other published reports detail the stereochemistry for other bafilomycins and other members of this class (O'Shea M. et al J. Antibiotics 50: 1073-1077, 1997). Molecules in this class have the same stereochemistry for the lactone ring, the tetrahydropyrin ring, and the C16-C18 linkage. All appear to possess a hydrogen-bonding network that includes C19OH, C17OH, and C1=O. This network effectively defines the configuration of the side chain. Based on the analysis of coupling constant, chemical shift, and Rotating Frame Overhauser Effect Spectroscopy (ROESY) data, the proposed stereochemistry of the compound of formula (I) is consistent with this conformation. The new hexadiene sidechain at C23 was assigned as alpha to the ring based on two key ROESY correlations. There is a correlation between H23 and CH$_3$-36 and also between H23 and H21. These correlations would be unlikely unless H23 was positioned above the ring.

TABLE 2

$^1$H and $^{13}$C NMR chemical shifts for the compound of formula (I)$^a$

| | $\delta_C$ (ppm) | M | $\delta_H$ (ppm) |
|---|---|---|---|
| 1 | 167.57 | s | |
| 2 | 141.97 | s | |
| 3 | 133.35 | d | 6.63(1H, s) |
| 4 | 132.74 | s | |
| 5 | 145.55 | d | 5.94(1H, d, 8.7) |
| 6 | 37.85 | d | 2.52(1H, m) |
| 7 | 80.17 | d | 3.28(1H, br d, J 5.4) |
| 8 | 41.93 | d | 1.86(1H, m) |
| 9 | 42.27 | t | 2.12(1H, m), 2.03(1H, m) |
| 10 | 144.98 | s | |
| 11 | 125.19 | d | 5.80(1H, d, 10.7) |
| 12 | 134.53 | d | 6.67(1H, dd, 15.0, 10.8) |
| 13 | 126.95 | d | 5.12(1H, m) |
| 14 | 82.98 | d | 4.07(1H, m) |
| 15 | 77.01 | d | 4.96(1H, dd, 8.4, 1.3) |
| 16 | 38.23 | d | 2.13(1H, m) |
| 17 | 70.80 | d | 4.11(1H, m) |
| 18 | 42.27 | d | 1.84(1H, m) |
| 19 | 100.26 | s | |
| 20 | 40.22 | t | 2.35(1H, dd, 11.7, 4.8), 1.34(1H, m) |
| 21 | 75.11 | d | 5.08(1H, m) |
| 22 | 41.81 | d | 1.50(1H, m) |
| 23 | 75.34 | d | 4.14(1H, m) |
| 24 | 130.81 | d | 5.50(1H, dd, 15.1, 7.6) |
| 25 | 133.51 | d | 6.18(1H, dd, 15.5, 15.4) |
| 26 | 129.72 | d | 5.99(1H, dd, 15.1, 10.5) |
| 27 | 137.21 | d | 5.70(1H, m) |
| 28 | 26.16 | t | 2.09(2H, m) |
| 29 | 13.73 | q | 0.97(3H, d, 2.8) |
| 30 | 14.13 | q | 1.94(3H, br s) |
| 31 | 17.62 | q | 1.03(3H, d, 7.0) |
| 32 | 22.20 | q | 0.90(3H, d, 6.8) |
| 33 | 20.33 | q | 1.93(3H, br s) |
| 34 | 10.02 | q | 0.85(3H, m) |
| 35 | 7.2 | q | 1.00(3H, d, 2.5) |
| 36 | 11.61 | q | 0.85(3H, m) |
| 2-OCH3 | 59.94 | q | 3.50(3H, s) |
| 14-OCH3 | 55.63 | q | 3.23(3H, s) |
| 1' | 168.14 | s | |
| 2' | 134.97 | d | 7.57(1H, d, 15.3) |
| 3' | 132.97 | d | 6.82(1H, d, 15.3) |
| 4' | 165.00 | s | |
| 5' | $^b$ | s | |
| 6' | $^b$ | s | |
| 7' | 27.75 | t | 2.52(2H, m) |
| 8' | 37.31 | t | 2.52(2H, m) |
| 9' | $^b$ | s | |

$^a\delta$ in ppm, J value in Hz. Data were recorded at 500 and 125 MHz, respectively in acetone-d$_6$.
$^b$Signal not observed.

Biological Activity

A panel of cell proliferation assays (referred to herein as "bioassays") based on the inhibition of cell proliferation in selected human tumour cell lines (mammary MCF-7, colon HT-29, leukemia K562/C1,000 and melanoma Malme-3M) was used to identify antiproliferative activities in the different samples throughout the purification procedures. Extracts from strain JS1035 grown in four different media were tested in bioassays; the one that contained most of the antiproliferative activity was selected for further study. A 1:1,000-dilution of the active extract resulted in an almost complete inhibition of cell proliferation in the three cell lines tested (melanoma Malme-3M cell line was omitted at this stage). From this initial crude extract, collected fractions from counter current partition chromatography were individually analyzed on MCF-7 cell proliferation. A major single fraction was shown to contain antiproliferative activity, which was then further purified by HPLC. A single HPLC peak was found to contain antiproliferative activities as measured by inhibition of cell proliferation in the bioassay. This peak was used to initiate structure elucidation of the active compound of formula (I). Subsequent structure work was completed using material isolated with two consecutive CPC steps.

Figure 1B:
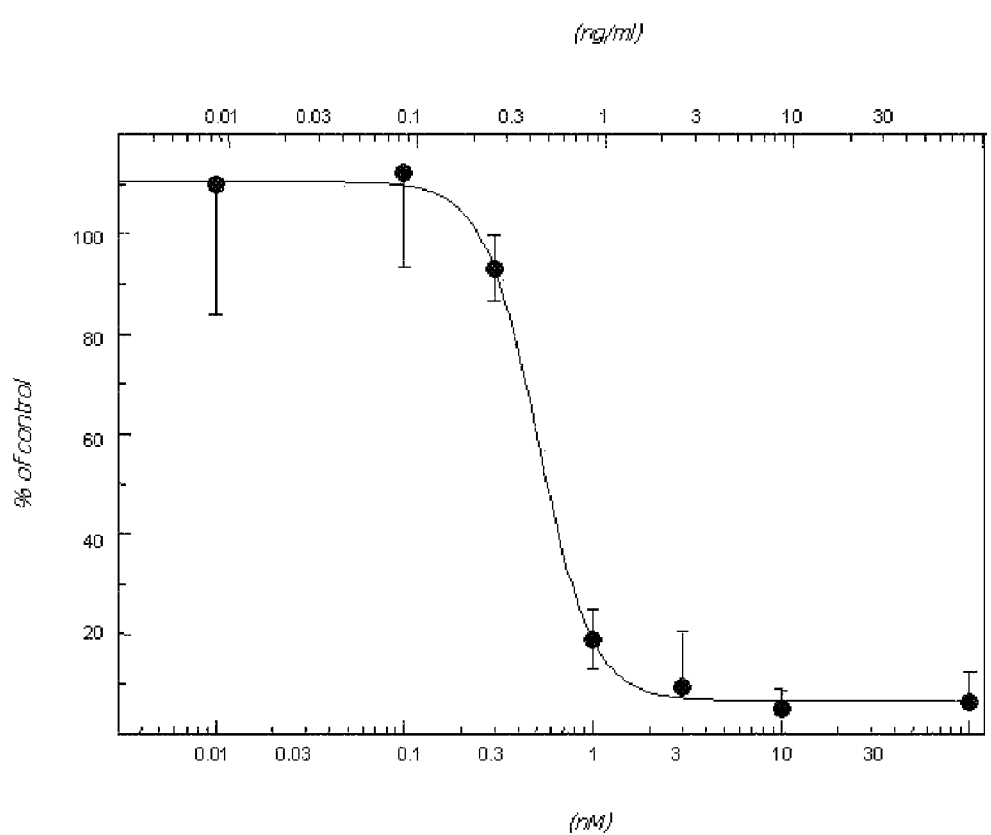
FIG. 1B: Dose-dependent inhibition of tumour cell proliferation (bioassay) by the compound of formula (I). Human HT-29 tumour cells were treated with indicated concentrations of the compound of formula (I) for 4 days. Results, expressed as % of control untreated cells, are the mean±SE of at least 3 different experiments.
Figure 1C:
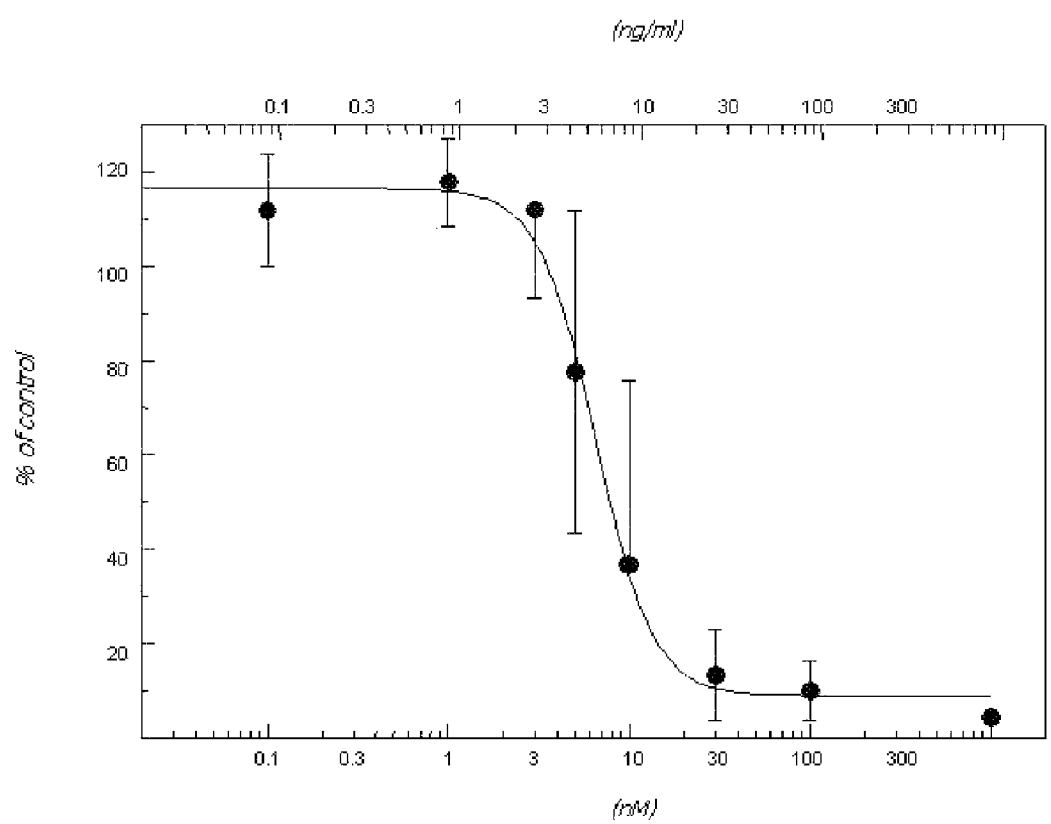
FIG. 1C: Dose-dependent inhibition of tumour cell proliferation (bioassay) by the compound of formula (I). Human K562/C1,000 tumour cells were treated with indicated concentrations of the compound of formula (I) for 4 days. Results, expressed as % of control untreated cells, are the mean±SE of at least 3 different experiments.
Figure 1D:
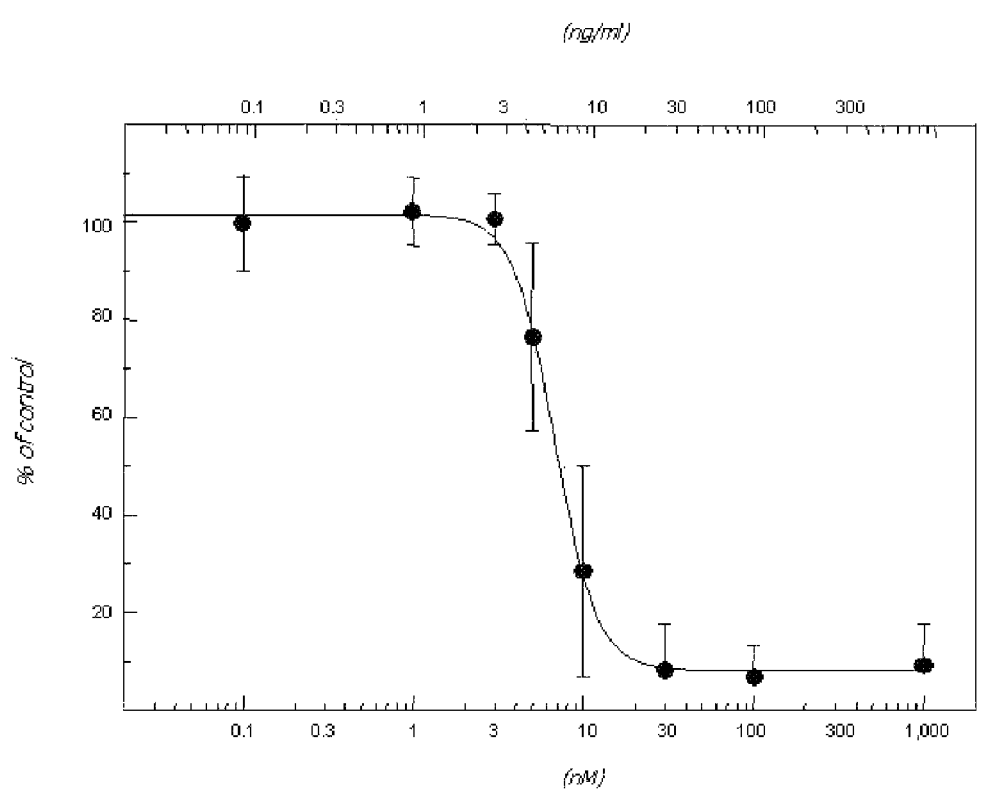
FIG. 1D: Dose-dependent inhibition of tumour cell proliferation (bioassay) by the compound of formula (I). Human Malme-3M tumour cells were treated with indicated concentrations of the compound of formula (I) for 4 days. Results, expressed as % of control untreated cells, are the mean±SE of at least 3 different experiments.

The purified compound of formula (I) was extensively characterized for its ability to inhibit tumour cell growth. As indicated in FIG. 1A-D, the dose-dependent inhibition of the compound of formula (I) in the four selected tumour cell proliferation assays was typical for classical cytotoxics, with very steep and narrow dose-response curves. The compound of formula (I) exhibited similar potency for inhibition of tumour cell proliferation in the nM range of concentrations, with a slightly higher activity on colon HT-29 carcinoma cells (sub-nanomolar concentrations) (Table 3). Initial observation on inhibition of tumour cell proliferation was extended to a wide variety of human tumour cell lines, from ovary, prostate, pancreas, colon and lung origins, with observed IC$_{50}$ values in the nM range of concentrations (Table 4).

The activity of the compound of formula (I) on P-glycoprotein- or Multidrug Resistant Protein-expressing tumour cell lines and respective parental cells, K562/C1,000+ and K562A7, COR-L23/R and COR-L23, was compared to that of a known substrate for P-glycoprotein/Multidrug Resistant Protein, adriamycin. As indicated in Table 5, the compound of formula (I) inhibited cell proliferation in the nM range of concentrations regardless of the P-glycoprotein and/or Multidrug Resistant Protein expression status (no significant difference between IC$_{50}$ values). On the contrary, K562/C1,000+ and CORL23/R cells exhibited a 250-fold and 20-fold resistance to cell killing by adriamycin, respectively, as compared to their respective parental cell lines. These results strongly suggested that there is no substantial recognition of the compound of formula (I) by the P-glycoprotein and Multidrug Resistant Protein pump proteins.

TABLE 3

Inhibition of tumour cell proliferation by the compound of formula (I). Sensitivity to cell killing by the compound of formula (I) was assessed in breast MCF-7, colon HT-29, leukemia K562/C1,000 and melanoma Malme-3M cells. Cell viability was determined after a 4-day incubation in the absence (control) or presence of increasing concentrations of the compound of formula (I). Results, means ± SE from at least three separate experiments, are expressed as IC$_{50}$ values (in nM).

| Cell Lines | Compound of formula (I) |
|---|---|
| MCF-7 | 1.92 ± 0.35 |
| HT-29 | 0.61 ± 0.04 |
| K562/C1,000 | 9.89 ± 7.35 |
| Malme-3M | 7.96 ± 2.73 |

TABLE 4

Effect of the compound of formula (I) on human tumour cell proliferation. Activity of the compound of formula (I) on tumour cell proliferation was assessed on several human tumour cell lines from various origins. As indicated in the Materials and Methods section, a 4-day incubation period in the absence (control) or presence of increasing concentrations of the compound of formula (I) was followed by cell viability determination using MTT staining method. Results, means ± SE from two separate experiments, are expressed as $IC_{50}$ values (in nM) which represent the concentration of compound required to inhibit cell proliferation by 50%.

| Cell Line | Tissue origin | Compound of formula (I) |
|---|---|---|
| A2780 | ovary | 1.37 ± 0.13 |
| DU 145 | prostate | 1.95 ± 0.30 |
| Capan-1 | pancreas | 6.93 ± 3.39 |
| HCT 116 | colon | 1.56 ± 0.03 |
| LoVo | colon | 5.98 ± 5.52 |
| H1299 | lung | 1.46 ± 0.13 |

TABLE 5

Is the compound of formula (I) a substrate for P-glycoprotein/Multidrug Resistant Protein? Sensitivity to cell killing by the compound of formula (I) and adriamycin was assessed in human K562A7 parental leukemia cells and P-glycoprotein overexpressing counterpart, K562/C1,000+ cells; as well as parental small cell carcinoma COR-L23 cells, and Multidrug Resistant Protein overexpressing counterpart, COR-L23/R cells. Cell viability was determined after a 4-day incubation in the absence (control) or presence of increasing concentrations of the compound of formula (I). Results, mean ± SE from at least two separate experiments, are expressed as $IC_{50}$ values (in nM).

| Cell Line | Compound of formula (I) | Adriamycin |
|---|---|---|
| K562A7 | 14.08 ± 1.25 | 26.78 ± 5.82 |
| K562/C1,000+ | 29.34 ± 1.80 | 7,829 ± 806 |
| COR-L23 | 5.13 ± 0.91 | 36.57 ± 19.09 |
| COR-L23/R | 6.90 ± 0.24 | 676 ± 261 |

Example 1

Structure Determination $^1$H and $^{13}$C NMR spectra were recorded at 300K on a Bruker Avance DRX 500 spectrometer operating at 500 and 125 MHz, respectively. Standard pulse sequences were used for DEPT, COSY, HMQC, and HMBC experiments. ROESY data was acquired using a spinlock pulse of 300,000 µs (at 22 dB). Melting points were determined using an Electrothermal 9100 melting point apparatus and are uncorrected. Inversion Recovery (IR) data was acquired using a Perkin Elmer 1600 Series FTIR spectrophotometer. A Perkin-Elmer 243B polarimeter was used to procure optical rotation data. High resolution MS data was obtained using a Micromass 70SEQ Tandem Hybrid Mass Spectrometer. CPC was performed on a P.C., Inc. high speed countercurrent chromatograph, equipped with an Ito multilayer coil column interfaced with a Waters 991 Photodiode Array detector (monitoring at 270 nm).

Fermentation and Isolation

The actinomycete strain JS1035 was isolated from river bottom sediment collected near Sombo, Cameroon. The seed medium contained glucose 20 g, Pharmamedia (Trader's Protein) 15.0 g, yeast extract 5.0 g, $CaCO_3$ 4.0 g, $(NH_4)_2(SO_4)$ 3.0 g, $ZnSO_4.7H_2O$ 0.03 g in 1 L distilled water, pH adjusted to 6.5. The production medium contained glucose 20.0 g, dextrin 50.0 g, Pharmamedia (Trader's Protein) 30.0, yeast extract 1.0 g, $CaCO_3$ 5.0 g, $CoCl_2.6H_2O$ 0.001 g in 1 L distilled water, pH adjusted to 7.0. The media were dispensed in 25 or 30 mL aliquots to 250 mL flasks and autoclaved for 15 min. Frozen spore stocks (1.0 mL) were used to inoculate starter cultures (25 mL seed media per 250 mL Erlenmeyer flask). Starter cultures were incubated at 28° C. and ~75% humidity on an orbital shaker (2" throw, 250 rpm) for 48 h. The starter cultures (1 mL) were used to inoculate 200 production media flasks (30 mL production media per 250 mL Erlenmeyer flask), which were then incubated for 6 days at the above conditions.

Ethyl acetate (22.5 mL) was added to each flask, and the flask contents were pooled into 500 mL centrifuge bottles. Each bottle was shaken vigorously and centrifuged at 6000×g for 8 minutes. The ethyl acetate was removed from each bottle and dried over anhydr. $Na_2SO_4$. Ethyl acetate was again added to the centrifuge bottles to a total volume of approximately 450 mL, and the process was repeated. The extract was dried under reduced pressure to yield a crude extract (5.4 g).

An aliquot (400 mg) of the crude extract was subjected to CPC. The solvent system consisted of an equilibrated mixture of n-hexane, EtOAc, MeOH, and water (1:3:3:3, v/v/v/v). The lower phase was used as the stationary phase, and the upper phase served as the mobile phase which was pumped at 3 mL/minute. The column rotation speed was 800 rpm. The crude extract was prepared by dissolving it in a mixture of upper and lower phases. The material was then loaded onto the column. The first peak to elute was collected and dried to yield 303 mg of purified material. This purified material was again subjected to CPC chromatography using modified conditions. The modified solvent system consisted of an equilibrated mixture of water, MeOH, and n-hexane (1:9:10, v/v/v). Again, the lower phase was used as the stationary phase, and the upper phase served as the mobile phase. After 90 minutes, the upper and lower phases were switched and the first peak to elute after the solvent change was collected and dried to yield 9.2 mg of the pure compound of formula (I).

Initially, the compound of formula (I) was isolated using HPLC following the first CPC separation. In that case, the active CPC fraction was further separated using reversed-phase HPLC (LiChrospher, 10 µm, 10×25 mm, $C_{18}$). A linear gradient starting at 95:5 $CH_3CN:H_2O$ to 100% $CH_3CN$ over 25 minutes was used to isolate the compound of formula (I). A 5-mg HPLC injection yielded 0.5 mg of compound (I).

Drugs

All samples tested were dissolved in DMSO and further dilutions (typically 1:1,000) were made in culture medium, with final DMSO concentrations never exceeding 0.1% (v/v) in cell proliferation assays. MTT [3-(4,5-dimethylthiazol-2-yl)-2,5-diphenyltetrazolium bromide], MTS [3-(4,5-dimethylthiazol-2-yl)-5-(3-carboxymethoxyphenyl)-2-(4-sulfophenyl)-2H-tetrazolium inner salt] and PMS [phenazine methosulfate] were dissolved in phosphate-buffered saline (PBS).

MTT and MTS are both tetrazolium salts widely used in cell proliferation and toxicity tests. Upon entry in a viable cell, these tetrazolium salts are (bio)reduced to an intensely colored formazan derivative. In case of MTT, the formed formazan is crystalline and needs to be dissolved before colorimetric quantification. MTS needs an intermediate electron acceptor (PMS) for its efficient reduction into a soluble formazan end product and is used for suspension cell lines.

Cell Lines and Cell Culture

The human MCF-7 mammary adenocarcinoma cells were cultured in Dulbecco's Modified Eagle Medium (DMEM) supplemented with 2 mM L-glutamine, 1 mM NaPyruvate, 50 µg/ml gentamicin and 5% fetal calf serum. The human HT-29 colon carcinoma cells were cultured in Mc Coy's 5a medium supplemented with 2 mM L-glutamine, 50 µg/ml gentamicin and 5% fetal calf serum. The human Malme-3M melanoma cells were cultured in DMEM medium supplemented with 2 mM L-glutamine, 1 mM NaPyruvate, 50 µg/ml gentamicin and 10% fetal calf serum. The human DU 145 prostate carcinoma cells were cultured in DMEM medium supplemented with 2 mM L-glutamine, 1 mM NaPyruvate, 50 µg/ml gentamicin and 10% fetal calf serum. The human Capan-1 pancreatic adenocarcinoma cells were cultured in DMEM medium supplemented with 2 mM L-glutamine, 1 mM NaPyruvate, 50 µg/ml gentamicin and 10% heat inactivated fetal calf serum. The human HCT 116 colorectal carcinoma cells were cultured in Mc Coy's 5a medium supplemented with 2 mM L-glutamine, 50 µg/ml gentamicin and 10% fetal calf serum. The human H1299 non-small lung carcinoma cells were cultured in RPMI 1640 medium supplemented with 2 mM L-glutamine, 1 mM NaPyruvate, 10 mM HEPES and 10% heat inactivated fetal calf serum. All these cell lines were obtained from ATCC [American Type Culture Collection, Manassas, Va., USA]. The human A2780 ovarian carcinoma cell line was a kind gift from Dr. T. C. Hamilton [Fox Chase Cancer Centre, Pennsylvania, USA] and was cultured in RPMI 1640 medium supplemented with 2 mM L-glutamine, 50 µg/ml gentamicin and 10% fetal calf serum. The human LoVo colon adenocarcinoma cell line was a kind gift from Dr. M. Grandi [Pharmacia-Fice, Nerviano, Milano, Italy] and was cultured in HAM's F12 medium supplemented with 2 mM L-glutamine, 50 µg/ml gentamicin, 1% Vitamins (BME) and 10% fetal calf serum. Cells were routinely kept as monolayer cultures at 37° C. in a humidified 5% $CO_2$ atmosphere. The human K562/C1,000 leukemia cell line was a kind gift by Dr. H. Heyligen [Dr. Willems Instituut, Diepenbeek, Belgium] and is a P-glycoprotein expressing cell line obtained by culturing the cells at increasing concentrations of colchicine. The cells were kept as a suspension culture at 37° C. in a humidified 5% $CO_2$ atmosphere in RPMI 1640 medium supplemented with 2 mM L-glutamine, 50 µg/ml gentamicin and 5% fetal calf serum. The human K562A7 leukemia cell line was a kind gift by Dr. H. Heyligen and is the parent, drug sensitive cell line of the K562/C1,000 cells. The K562/C1,000+ cell line was obtained by culturing the K562/C1,000 cells for an additional 2 weeks with 1 µM colchicine. This treatment induces higher levels of P-glycoprotein and mRNA and a more stable resistance profile. The cells were kept as a suspension culture at 37° C. in a humidified 5% $CO_2$ atmosphere in RPMI 1640 medium supplemented with 2 mM L-glutamine, 50 µg/ml gentamicin and 5% fetal calf serum. The human large cell lung cancer cell lines were obtained from ECACC (European Collection of Cell Cultures, Salisbury, U.K.). COR-L23 is the parent, drug sensitive cell line and COR-L23/R is the Multidrug Resistant Protein-expressing Multidrug Resistant-variant, developed by continuous step-wise in vitro incubation of COR-L23 cells with increasing concentrations of doxorubicin. The culture medium for both cell lines consisted of RPMI 1640 supplemented with 2 mM L-glutamine, 50 µg/ml gentamicin and 10% fetal calf serum. Cells were routinely kept as monolayer cultures at 37° C. in a humidified 5% $CO_2$ atmosphere.

All media and supplements were obtained from Life Technologies, Merelbeke, Belgium. Cells were free of mycoplasma contamination as determined using the Gen-Probe Mycoplasma Tissue Culture kit [BioMérieux, Brussel, Belgium].

Cell Proliferation Assays

Cell proliferation assays were performed as described (A critical assessment of the use of microculture Tetrazolium assays to measure cell growth and function (Mosmann, T. J. Immunol. Meth 65: 55-63, (1983)).

In case of adherent cell lines, cells were seeded in Falcon/NUNC 96-well culture plates [Life Technologies, Merelbeke, Belgium] and allowed to adhere to the plastic for 18-48 hr. Medium was then changed and drugs and/or solvents were added. Following 4-day incubation, cell density was assessed using a MTT-based assay measuring absorbance at 540 nm using a Emax 96-well spectrophotometer [Sopachem, Brussel, Belgium]. For the experiments with the suspension culture, K562A7, K562/C1,000 and K562/C1,000+ cells were seeded in Falcon® 96-well culture plates. Test drugs and/or medium were added immediately after seeding. Following 4-day incubation, cell growth was assessed using a MTS/PMS based assay measuring absorbance at 490 nm using an Emax 96-well spectrophotometer.

The antiproliferative activity is calculated as percentage of remaining viable cells in treated versus control (untreated cells) conditions. Results are expressed as $IC_{50}$ values which represent the concentration of compound required to inhibit cell proliferation by 50%. Within an experiment, the result for each experimental condition is the mean of at least 3 replicate wells.

The invention claimed is:

1. An isolated microorganism *Micromonospora* spp. JS1035.

2. The microorganism of claim 1, wherein said microorganism is deposited under deposit No. LMG P-21525.

* * * * *